(12) United States Patent
Li et al.

(10) Patent No.: US 10,695,189 B2
(45) Date of Patent: Jun. 30, 2020

(54) INTERSPINOUS OMNIDIRECTIONAL DYNAMIC STABILIZATION DEVICE

(71) Applicant: BIODA DIAGNOSTICS (WUHAN) CO., LTD., Wuhan (CN)

(72) Inventors: Zhaowen Li, Wuhan (CN); Wensheng Guo, Wuhan (CN)

(73) Assignee: Bioda Diagnostics (Wuhan) Co., Ltd., Wuhan (CN)

( * ) Notice: Subject to any disclaimer, the term of this patent is extended or adjusted under 35 U.S.C. 154(b) by 0 days.

(21) Appl. No.: 15/540,228

(22) PCT Filed: Oct. 19, 2016

(86) PCT No.: PCT/CN2016/102584
§ 371 (c)(1),
(2) Date: Jun. 27, 2017

(87) PCT Pub. No.: WO2017/067461
PCT Pub. Date: Apr. 27, 2017

(65) Prior Publication Data
US 2018/0008429 A1    Jan. 11, 2018

(30) Foreign Application Priority Data

Oct. 21, 2015 (CN) .......................... 2015 1 0681705
Apr. 8, 2016 (CN) .......................... 2016 1 0215310
Aug. 15, 2016 (CN) .......................... 2016 1 0667104

(51) Int. Cl.
*A61B 17/70* (2006.01)
*A61F 2/44* (2006.01)
*A61F 2/30* (2006.01)

(52) U.S. Cl.
CPC ........ *A61F 2/4425* (2013.01); *A61B 17/7047* (2013.01); *A61B 17/7059* (2013.01);
(Continued)

(58) Field of Classification Search
CPC ........................................ A61B 17/7062–7071
See application file for complete search history.

(56) References Cited

U.S. PATENT DOCUMENTS 5,645,599 A * 7/1997 Samani .............. A61B 17/7062
606/248
6,440,169 B1 * 8/2002 Elberg ............... A61B 17/7062
623/17.11
(Continued)

FOREIGN PATENT DOCUMENTS

CN    101854872 A    10/2010
CN    102551855 A    7/2012
(Continued)

OTHER PUBLICATIONS

European search report from Application No. 16856892.1 dated Jul. 11, 2018, 9 pages.

*Primary Examiner* — Nicholas J Plionis
*Assistant Examiner* — Steven J Cotroneo
(74) *Attorney, Agent, or Firm* — Weisun Rao; Jun Chen; Venture Partner, LLC

(57) ABSTRACT

The present disclosure relates to an interspinous omnidirectional dynamic stabilization device, including a first fixing part, a second fixing part, a connecting structure and an elastic structure. The first fixing part and the second fixing part are fixedly connected to each other through the connecting structure and elastic structure. The bottoms of the first fixing part and the second fixing part are provided with one or more barbs. The elastic structure is made up of one or more U-shaped structures connected to each other. The first fixing part and the second fixing part are provided with fixing holes respectively.

3 Claims, 7 Drawing Sheets

(52) U.S. Cl.
CPC ............... *A61B 17/7062* (2013.01); *A61F 2002/30014* (2013.01); *A61F 2002/30069* (2013.01); *A61F 2002/30131* (2013.01); *A61F 2002/30291* (2013.01); *A61F 2002/30635* (2013.01); *A61F 2002/30841* (2013.01); *A61F 2002/30904* (2013.01); *A61F 2002/443* (2013.01)

(56) References Cited

U.S. PATENT DOCUMENTS

| | | | | |
|---|---|---|---|---|
| 8,834,482 | B2* | 9/2014 | Trautwein | A61B 17/7062 606/248 |
| 8,974,498 | B2* | 3/2015 | Beger | A61B 17/701 606/255 |
| 2005/0203624 | A1* | 9/2005 | Serhan | A61B 17/7062 623/17.11 |
| 2006/0271044 | A1* | 11/2006 | Petrini | A61B 17/7071 623/13.11 |
| 2006/0293662 | A1* | 12/2006 | Boyer, II | A61B 17/1671 606/249 |
| 2008/0109082 | A1* | 5/2008 | Fink | A61B 17/7062 623/17.16 |
| 2008/0167657 | A1* | 7/2008 | Greenhalgh | A61B 17/7065 606/90 |
| 2008/0183211 | A1* | 7/2008 | Lamborne | A61B 17/7068 606/249 |
| 2008/0228225 | A1* | 9/2008 | Trautwein | A61B 17/1606 606/246 |
| 2008/0269904 | A1* | 10/2008 | Voorhies | A61B 17/7026 606/86 A |
| 2008/0281423 | A1* | 11/2008 | Sheffer | A61B 17/7062 623/17.11 |
| 2009/0270919 | A1* | 10/2009 | Dos Reis, Jr. | A61B 17/7062 606/249 |
| 2009/0292314 | A1* | 11/2009 | Mangione | A61B 17/7062 606/249 |
| 2010/0036419 | A1* | 2/2010 | Patel | A61B 17/7065 606/249 |
| 2010/0191287 | A1* | 7/2010 | Bucci | A61B 17/7062 606/249 |
| 2010/0204732 | A1 | 8/2010 | Aschmann et al. | |
| 2011/0040330 | A1* | 2/2011 | Sheffer | A61B 17/7062 606/249 |

FOREIGN PATENT DOCUMENTS

| | | |
|---|---|---|
| CN | 203988504 U | 12/2014 |
| CN | 293988502 U | 12/2014 |
| CN | 204092151 U | 1/2015 |
| CN | 104323846 A | 2/2015 |
| CN | 104799928 A | 7/2015 |
| CN | 104873258 A | 9/2015 |
| CN | 104921793 A | 9/2015 |
| CN | 204708959 U | 10/2015 |
| CN | 105193524 A | 12/2015 |
| CN | 265126504 U | 4/2016 |
| TW | 200920306 A | 5/2009 |
| WO | 2014195535 A1 | 12/2014 |

* cited by examiner

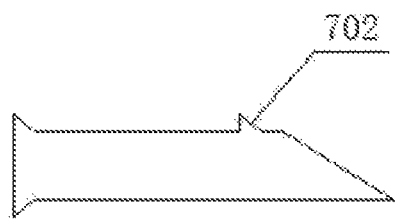
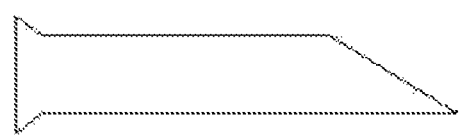
FIG. 20　　　　　　　　　　　FIG. 21
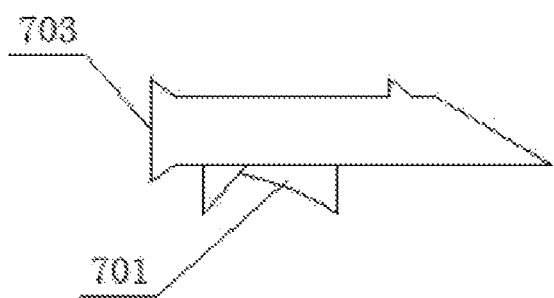
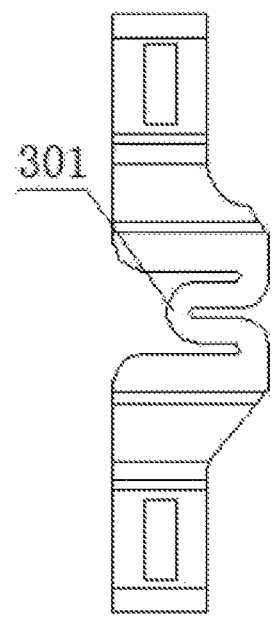
FIG. 22　　　　　　　　　　　FIG. 23

INTERSPINOUS OMNIDIRECTIONAL DYNAMIC STABILIZATION DEVICE

REFERENCE TO RELATED APPLICATIONS

The application is a U.S. national phase application of international application No. PCT/CN2016/102584, filed on Oct. 16, 2016, which claims priority to Chinese application No. 201510681705.9, filed on Oct. 21, 2015, Chinese Application No. 201610215310.4, filed on Apr. 8, 2016, and Chinese Application No. 201610667104.7, filed on Aug. 15, 2016, the contents of all of which are incorporated herein in their entireties.

FIELD OF THE INVENTION

The present invention relates generally to the technical filed of implantation of a medical device into human body, and more particularly, to an interspinous omnidirectional dynamic stabilization device.

BACKGROUND OF THE INVENTION

At present, the spinal fusion technology has obtained a good curative effect on treating neck and waist pain, and cervical vertebra and lumbar vertebra instability, with a fusion rate above 90%. However, many studies have shown that accelerated adjacent segment degeneration, fixation failure, pseudoarticulation formation or other complications may occur after rigid internal fixation or spinal fusion. For this reason, spine dynamic stabilization is becoming a hot technology for treating retrograde degeneration of cervical vertebra and lumbar vertebrae in recent years, and is one of the important developing trends of spine surgery, including five types, such as artificial or total disc replacement, artificial nucleus replacement, transpedicular dynamic neutralization system, interspinous dynamic stabilization device and facet joint formation device. Among these technologies, the interspinous dynamic stabilization device may be minimally invasive during implantation, with highest safety and simplest operation, and may cause minor complications, if any. That is, even if it fails, further surgery may not be influenced. As such, interspinous dynamic stabilization devices have been developing rapidly in recent years.

The implantation of an interspinous dynamic stabilization device has the following advantages. The device may be dynamically stabilized without reducing the immediate stability of the spine, and may disperse the load transmission of the rigid internal fixation to avoid stress shielding. The distraction force of intervertebral distraction may generate an opposite kyphosis on the surgical segment, to expand the inflected ligamenta flava reversedly to reduce the intrusion into the spinal canal, increasing the spinal canal volume. The device may also restore the height of intervertebral space, increase the cross-sectional area of the spinal canal and the opening area of the intervertebral foramen, increase the load of the annulus fibrosus after unloading, reduce the load of the facet joint on the corresponding segment. In addition, with this device, the patient may recover quickly after surgery, with a low recurrence rate, and the symptom such as pain may be significantly relieved, so that the patient may get out of bed earlier to resume normal activities.

However, there are still many defects in the traditional interspinous dynamic stabilization device. For example, the devices may not match the spinous anatomy, hit the spine to cause wear, or be quite complicated in structure. And the traditional device may be too large that the wound during surgery is large and the device is difficult to install and take up much space in the body after operation. In addition, there is a risk of disengagement when the traditional device is stabilized by an assembly, and there is a risk of loosening when the traditional device is stabilized by a binding belt. During the installation of the traditional device, the prosthesis may be required to be close to the spinal dura mater, which increases the surgical difficulty and risk of damaging the spinal dura mater. Further, the elastic structure in the traditional device may show poor elasticity and poor vertical support, and the traditional device has a weak ability of elasticity attenuation resistance after the operation, so it is difficult to ensure low incidence of complications and good long-term effect.

For example, the Coflex system designed and developed by Samani et al. in 1994 is U-shaped when viewed from the side, upper and lower ends of the U-shaped main structure having two "clamp-shaped" fixed wings (in which one is anterior, and the other is posterior) for clamping and fastening upper and lower spinous processes. However, the part of the system to be fastened to the spinous process is a square structure which does not match the spinous anatomy of the spinous process, and in this case, the side wings should be stretched and deformed greatly with a forceps during the surgery, and the side wings should be shut together after the surgery, so the installation of such system is complicated, and the side wings are easy to be fatigue and broken. In addition, such system may only provide sagittal extension and flexion. Chinese Patent No. 201020247832.0 discloses a "spinal nonfusion stabilization device" with substantially the same configuration as the Coflex system. Specifically, in this device, the U-shaped part 1 corresponds to the U-shaped main structure in the Coflex system, front and back fixation plates 2 corresponds to the two "clamp-shaped" fixed wings in the Coflex system, and the front and back fixation plates 2 are fastened to two adjacent spinous processes with screws, to achieve the fixation of the U-shaped main structure. However, as mentioned above, such device may only implement sagittal extension and flexion. That is, the size of the opening end of the U-shaped structure may be changed as the deformation of the U-shaped structure, so that the size of the opening end can match the variation in the distance between the spinous processes. Such U-shaped structure shows poor vertical support. In addition, its barb is relatively far away from the bottom of the U-shaped structure, and the location to which the barb is fastened is far away from the root of the spinous process when the bottom of the U-shaped structure is not close to the spinal dura mater, so the fixation effect would be affected.

The applicant of the present application has filed a Chinese patent application No. 201520426702.6, entitled "interspinous stabilization device". In clinical applications of the device, the prosthesis is unable to be inserted into a depth close to the dura mater during the surgery due to the large size of the device, so the rotation center of the prosthesis is relatively far away from the rotation center of the lumbar spine when the lumbar spine is twisted, that is, when the lumbar spine moves coronal direction. In addition, it is complicated in fixation with screws, and there is risk of the loosening of the screws. Moreover, the lateral mobility of the device is too large, increasing a new destabilizing factor to the lumbar vertebra.

A perfect interspinous dynamic stabilization device should generate permanent, sufficient distraction force at the bottom of the spinous process after implantation, to restore the height of intervertebral space, increase the opening area of the intervertebral foramen, expand the inflected ligamenta flava reversedly to reduce the intrusion into the spinal canal, and increase the volume of the spinal canal, while allowing the spine to maintain good dynamical activities, such as extension and flexion, for a long period of time. However, the previous interspinous dynamic stabilization devices are generally not able to have both good, persistent vertical distraction force and versatile mobility.

SUMMARY OF THE INVENTION

An objective of the present disclosure is to provide an interspinous omnidirectional dynamic stabilization device, to overcome the above defects in the prior art. The interspinous omnidirectional dynamic stabilization device is able to provide the maximum matching for the mobility in all directions, according to the requirements on the physiological activities of the human body, without causing stabilizing structures to be relatively displaced, or loosen and fall off. In addition, the device has a reasonably designed structure, with a small size. The device can be firmly fixed, and have a strong ability of elasticity attenuation resistance. In the device, the prosthesis has strong vertical support force at the bottom of the spinous process after implantation. Moreover, the device is fixed to the spinous processes and lamina, with the elastic structure attached to the spinous processes on either side of an interspinous space, and the bottom of the prosthesis is not forced to be close to the spinal dura mater. Both the coronal and sagittal rotation centers of the prosthesis are close to the coronal and sagittal rotation centers of the spine respectively, which is beneficial for recovery of a patient from operation.

The objective of the present disclosure can be achieved by the following technical solutions.

An interspinous omnidirectional dynamic stabilization device is provided, including a first fixing part, a second fixing part, a connecting structure and an elastic structure, wherein the first fixing part and the second fixing part are fixedly connected to each other through the connecting structure and elastic structure, the bottoms of the first fixing part and the second fixing part are provided with one or more barbs, the elastic structure is made up of one or more U-shaped structures connected to each other, and the first fixing part and the second fixing part are provided with fixing holes respectively.

Further, one end or both ends of an inner side of the first fixing part are provided with first clamping teeth, one end or both ends of an inner side of the second fixing part are provided with second clamping teeth, and first clamping teeth and the second clamping teeth extend in a direction parallel to and/or perpendicular to a longitudinal direction of a spinous process.

Further, the first fixing part and the second fixing part can be an integrative structure as above, or a combinatorial structure. The combinatorial structure is provided as below. The first fixing part includes two first side wings, a base plate and a first fastening structure, the two first side wings are movably connected to the base plate through the first fastening structure, the first clamping teeth are arranged on an inner side of each first side wing, the fixing hole is arranged on an end of each first side wing, the barb is arranged on the base plate, and a lower side of each first side wing is provided with a first curved protrusion. The second fixing part includes two second side wings, a curved base plate and a second fastening structure, the two second side wings are movably connected to the curved base plate through the second fastening structure, the second clamping teeth are arranged on an inner side of each second side wing, the fixing hole is arranged on an end of each second side wing, the barb is arranged on the curved base plate, and a lower side of each second side wing is provided with a second curved protrusion.

The above first and second fixing parts can also be two semi-U-shaped structures. Each semi-U-shaped structure is provided with a through inserting hole, the direction of the inserting hole is perpendicular to or not perpendicular to an external surface of the first fixing part or the second fixing part, a movable plate is mounted within the inserting hole, the movable plate is provided with a prefabricated anti-receding plate, a screw hole and a convex tooth, the convex tooth is arranged on any side of the movable plate, the movable plate has a head end formed as a slope surface, the slope surface is provided with inserting teeth, the movable plate has a tail end provided with a boss, the boss is arranged on any side of the movable plate, the convex tooth of the movable plate is adapted to abut against an inner surface of each of the first fixing part and the second fixing part when being implanted into a human body, the movable plate is adapted to be further inserted into the inserting hole during operation, and screws are adapted to be screwed into the screw hole or the prefabricated anti-receding plate is adapted to be bent with a bender to prevent the movable plate from receding; and when the movable plate is formed into a cone without a convex tooth, the movable plate is not mounted within the inserting hole in advance, and is adapted to be inserted into the inserting hole during operation, and screws are adapted to be screwed into the screw hole or the prefabricated anti-receding plate is adapted to be bent with a bender to prevent the movable plate from receding.

Further, the U-shaped structure is internally provided with a circular or arc structure, the U-shaped structure has a straight portion with a length within a range from 0 to 15 mm, and when the length of the straight portion is 0 mm, the U-shaped structure is replaced with a circular or arc structure.

Further, the U-shaped structure includes a vertical U-shaped structure with an opening formed upwardly or downwardly, a horizontal U-shaped structure with an opening formed inwardly or outwardly, a combination of the vertical U-shaped structure and the horizontal U-shaped structure, or a horizontal U-shaped structure formed by a concave arc or convex arc connected by sides of one or more vertical U-shaped structures, with an opening formed inwardly or outwardly.

Further, the elastic structure includes a spring, both ends of the spring are connected to two sides between the first fixing part and the second fixing part respectively, or connected to the middle between the first fixing part and the second fixing part, or connected to the U-shaped structure, or one end of the spring is connected to the U-shaped structure, and the other end of the spring is connected to the first fixing part or the second fixing part.

Further, the connecting structure is selected from the group consisting of plate-type structure, column-type structure, spring structure, and helical structure, the connecting structure has a length within a range from 0 to 8 mm, and when the connecting structure has a length of 0 mm, the first fixing part and the second fixing part are fixedly connected to each other through the elastic structure directly.

Further, the connecting structure is in a form made up of a holder and a connecting plate, the holder is arranged at the middle of the first fixing part, the holder is in hollow structure, the connecting plate is arranged at the middle of the second fixing part, a distal end of the connecting plate is provided with a screw hole or grooved portion, the holder is provided with a screw hole or slotted hole, there are two pairs of the holder and the connecting plate, the screw hole of the connecting plate corresponds to the crew hole of the holder when the connecting plate is inserted into the holder, and the connecting plate and the holder are connected and integrated by a screw, alternatively, the connecting plate is fastened to the holder by inserting the connecting plate into the holder, and inserting a bender through the slotted hole in the holder to bend and deform the grooved portion on the connecting plate, the first fixing part and the second fixing part in semi-U-shape form an entire U-shaped structure after connection, and the barb of the first fixing part is hooked at the root of the spinous process.

Further, each U-shape structure has a same or different height, size, plate thickness or distance between plates, and plates on both sided of each U-shape structure are parallel or not parallel to each other.

Further, different portions of the first fixing part has a same or different thickness or height, different portions of the second fixing part has a same or different thickness or height, the first and second fixing parts have a same or different thickness or height, and plates of the first and second fixing parts have a same or different thickness or height.

Further, a portion of the first or second fixing part attached to the spinous process or vertebral laminae is a flat plane or a curved plane.

Further, surfaces of both the first and second parts are coated with a material to induce the formation of bone therein, or processed to be porous or threaded.

Compared with the prior art, the present disclosure has the following advantages.

1. The interspinous omnidirectional dynamic stabilization device according to the present disclosure considers the needs of the physiological activities of the human body fully, and achieves the interspinous resilient distraction and the spine movement such as extension and flexion by the U-shaped structure or combinatorial U-shaped structure in the elastic structure and the connecting structure. In addition, the device can achieve the elastic dynamic stabilization of the operated spinal segment in a movement of flexion, extension, lateral curvature and rotation, and also achieve the dynamic stabilization of the operated spinal segment in a movement of circumduction formed by an combined action of movements in various directions and orientations, to maximize the matching of the mobility in each direction to the human body.

2. In the interspinous omnidirectional dynamic stabilization device according to the present disclosure, the first and second fixing parts can either be made to an integrative structure, or be made to a separated type combinatorial structure, without causing stabilizing structures to be relatively displaced, or loosen and fall off.

3. In the interspinous omnidirectional dynamic stabilization device according to the present disclosure, the first and second fixing parts can be made into two semi-U-shaped structures which can be connected into a whole by the holder and the connecting plate, and can be further fastened to the spinous process or vertebral plate by the movable plate, to avoid removing or cutting the supraspinal ligament during surgery.

4. In the interspinous omnidirectional dynamic stabilization device according to the present disclosure, the first and second fixing part are provided with at least one barb, and the barb can be fastened to the root of the spinous process to play a good role in fixation.

5. The interspinous omnidirectional dynamic stabilization device according to the present disclosure is also characterized by the reasonability of structure design, the small volume, the stress dispersion, the convenience of implantation, and the reliability of the fixation, and the strong ability of elasticity attenuation resistance, and both the coronal and sagittal rotation centers of the prosthesis are close to the coronal and sagittal rotation centers of the spine respectively after implantation, which is beneficial for recovery of a patient from operation.

6. The interspinous omnidirectional dynamic stabilization device according to the present disclosure addresses the problems that the previous interspinous dynamic stabilization devices are not available for cases where the intervertebral space is relatively small, the bottom of the prosthesis should be close to the spinal dura mater for installing, and also addresses the problem that the previous interspinous dynamic stabilization devices cannot achieve the interspinous elastic bearing capacity fully, the elastic structure shows poor elasticity, and the ability of elasticity attenuation resistance does not last long.

BRIEF DESCRIPTION OF THE DRAWINGS

FIG. 20 is a top view of the movable plate according to Example Three of the present disclosure.

FIG. 21 is a top view of a movable plate without a convex tooth according to Example Three of the present disclosure.

FIG. 22 is a top view of a bent and deformed prefabricated anti-receding plate of the movable plate according to Example Three of the present disclosure.

FIG. 23 is a schematic diagram illustrating a U-shaped structure with a shot length according to Example Three of the present disclosure.

DESCRIPTION OF REFERENCE SIGNS

Figure 1:
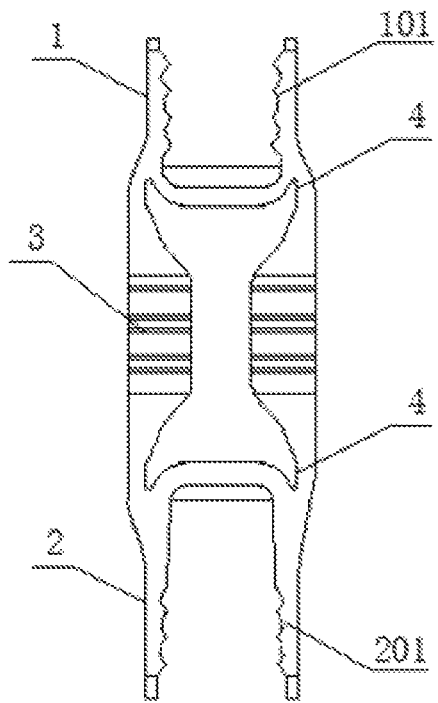
FIG. 1 is a front view of an interspinous omnidirectional dynamic stabilization device according to Example One of the present disclosure.

1: first fixing part; 101: first clamping tooth; 102: first curved protrusion; 103: first side wing; 104: base plate; 105: first fastening structure; 106: inserting hole; 2: second fixing part; 201: second clamping tooth; 202: second curved protrusion; 203: second side wing; 204: cured base plate; 205: second fastening structure; 3: elastic structure; 301: U-shaped structure; 302: spring; 4: connecting structure; 401: holder; 402: connecting plate; 403: screw hole or slotted hole; 404: screw hole or grooved portion; 5: fixing hole; 6: stab; 7: movable plate; 701: prefabricated anti-receding plate; 702: screw hole and convex tooth; 703: boss; and 704: inserting tooth.

DETAILED DESCRIPTION OF THE INVENTION

In the following description of embodiments, reference is made to the accompanying drawings which form a part hereof, and in which it is shown by way of illustration specific embodiments of the present invention that can be practiced. It is to be understood that other embodiments can be used and structural changes can be made without departing from the scope of the disclosed embodiments.

Example One

As shown in FIGS. 1-5, the interspinous omnidirectional dynamic stabilization device includes a first fixing part 1, a second fixing part 2, a connecting structure 4 and an elastic structure 3. The first fixing part 1 and the second fixing part 2 are fixedly connected to each other through the connecting structure 4 and elastic structure 3, the bottoms of the first fixing part 1 and the second fixing part 2 are provided with one or more barbs 6, the elastic structure 3 is made up of one or more U-shaped structures 301 connected to each other, and the first fixing part 1 and the second fixing part 2 are provided with fixing holes 5 respectively. The direction of the fixing hole 5 is perpendicular to or not perpendicular to an external surface of the first fixing part 1 and the second fixing part 2.

Further, both ends of an inner side of the first fixing part 1 are provided with first clamping teeth 101, both ends of an inner side of the second fixing part 2 are provided with second clamping teeth 201, and first clamping teeth 101 and the second clamping teeth 201 extend in a direction parallel to and/or perpendicular to a longitudinal direction of a spinous process.

Figure 4:
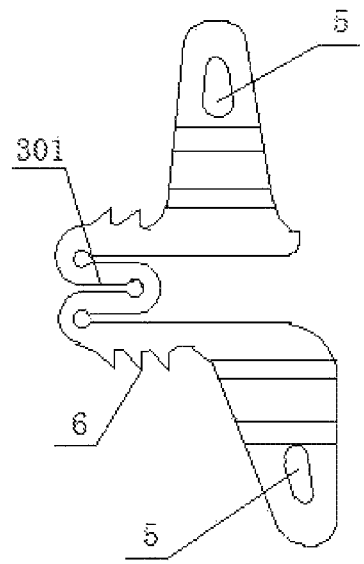
FIG. 4 is a side view showing the elastic structure connected to the first and second fixing parts directly according to Example One of the present disclosure.
Figure 5:
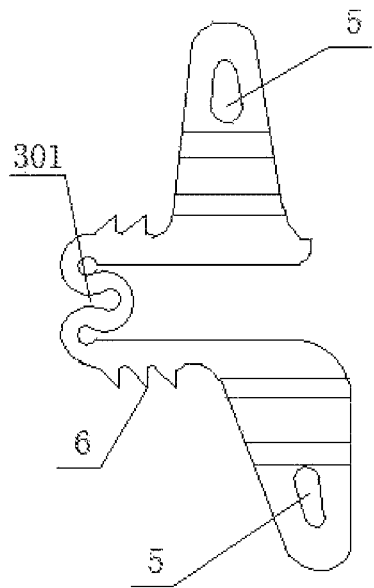
FIG. 5 is a structural schematic diagram illustrating the elastic structure as a circular or arc structure according to Example One of the present disclosure.

Further, as shown in FIG. 4, the U-shaped structure 301 is internally provided with a circular or arc structure, the U-shaped structure 301 has a straight portion with a length within a range from 0 to 15 mm. As shown in FIG. 5, when the length of the straight portion is 0 mm, the U-shaped structure 301 is replaced with a circular or arc structure.

Further, the U-shaped structure 301 includes a vertical U-shaped structure with an opening formed upwardly or downwardly, a horizontal U-shaped structure with an opening formed inwardly or outwardly, a combination of the vertical U-shaped structure and the horizontal U-shaped structure, or a horizontal U-shaped structure formed by a concave arc or convex arc connected by sides of one or more vertical U-shaped structures, with an opening formed inwardly or outwardly.

Figure 2:
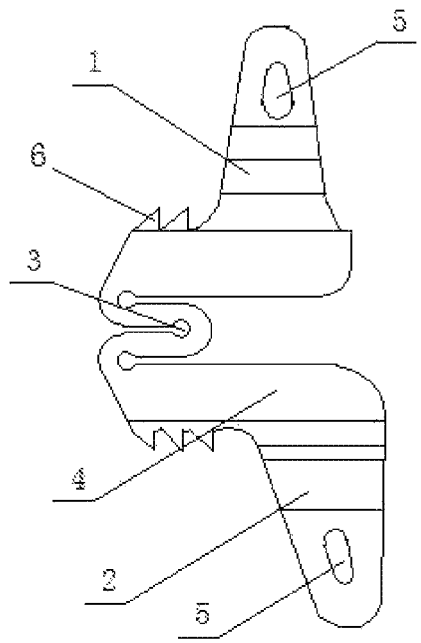
FIG. 2 is a side view of the interspinous omnidirectional dynamic stabilization device according to Example One of the present disclosure.
Figure 3:
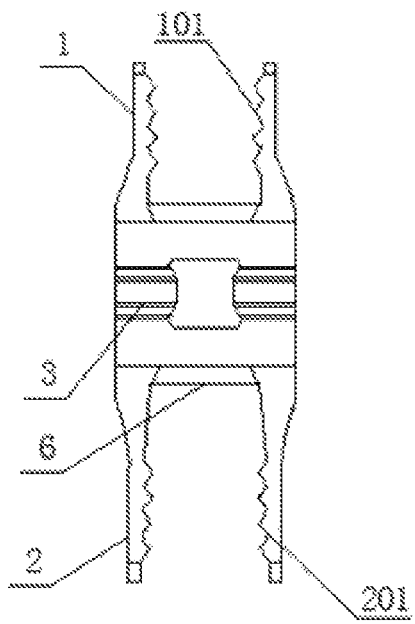
FIG. 3 is a front view showing an elastic structure connected to first and second fixing parts directly according to Example One of the present disclosure.

As shown in FIGS. 1-2, the connecting structure 4 may be a plate-type structure, a column-type structure, a spring structure, or a helical structure. The connecting structure 4 has a length within a range from 0 to 8 mm. As shown in FIGS. 3-4, when the connecting structure 4 has a length of 0 mm, the first fixing part 1 and the second fixing part 2 are fixedly connected to each other through the elastic structure 3 directly.

When the interspinous omnidirectional dynamic stabilization device in this example is to be implanted in to the body of a patient suffered from a degenerative cervical or lumbar vertebra disease, the supraspinal and interspinal ligaments may be incised to reshape the sclerotin of the spinous process firstly, and upper and lower processes are retracted to increase the intervertebral space. Then the mold is tested. If the test is successful, the first fixing part 1 and the second fixing part 2 may be inserted into a suitable position from the tail of the spinous process to the root of the spinous process. The two side wings may be clamped to abut against the sclerotin on both sides of the spinous process. The first fixing part 1 and the second fixing part 2 may be fastened to the spinous process and/or supraspinal ligament by medical suture or screw passing through the fixing holes 5 and holes drilled in the spinous process, to complete the installation.

With the elastic structure 3 and the connecting structure 4, the interspinous resilient distraction and the spine movement such as extension and flexion can be achieved, and the elastic movement of the operated segment such as lateral curvature and rotation can also be achieved. The device is not forced to be close to the spinal dura mater during the implantation. The surgery time is short, with high security. The device is applicable for cases where the intervertebral space is relatively small. The elastic structure 3 shows strong elasticity when being deformed during the spine movement after surgery, and the elastic structure 3 has strong vertical support and ability of elasticity attenuation resistance.

Example Two

In this example, the first fixing part 1 and the second fixing part 2 are connected and integrated to each other through the elastic structure 3 directly, and both the first fixing part 1 and the second fixing part 2 are flexibly removable structures.

As shown in FIGS. 6-12, the interspinous omnidirectional dynamic stabilization device includes a first fixing part 1, a second fixing part 2 and an elastic structure 3. The first fixing part 1 is connected and integrated to the second fixing part 2 through the elastic structure 3 directly. Since the adjacent upper and lower spinous processes may have different dimensions and shapes, the first fixing part 1 and the second fixing part 2 may be asymmetric structures, or symmetric structures, which facilitates the matching with the sclerotin of the spinous process.

Figure 6:
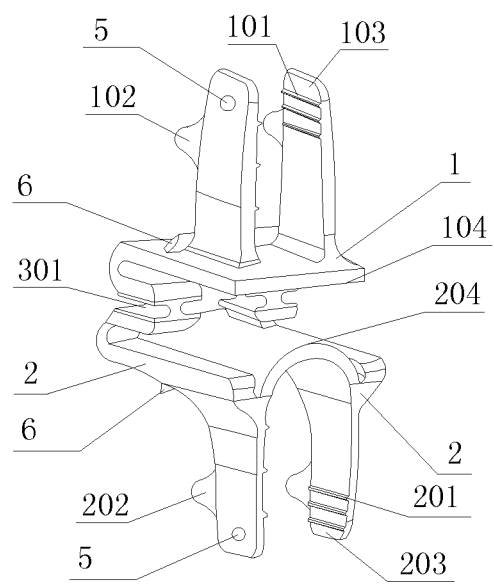
FIG. 6 is a perspective view of an interspinous omnidirectional dynamic stabilization device according to Example Two of the present disclosure.
Figure 7:
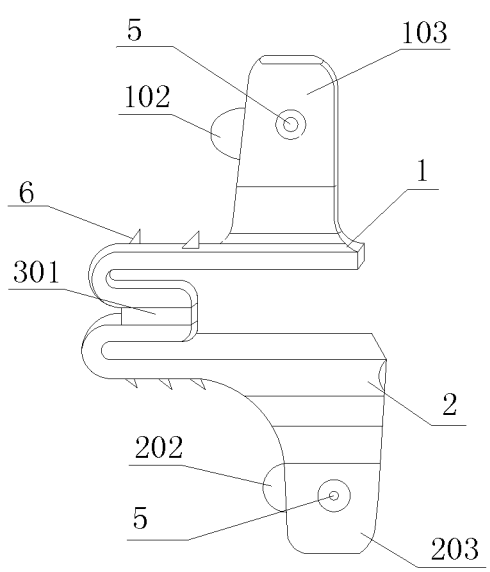
FIG. 7 is a left view of the interspinous omnidirectional dynamic stabilization device according to Example Two of the present disclosure.
Figure 8:
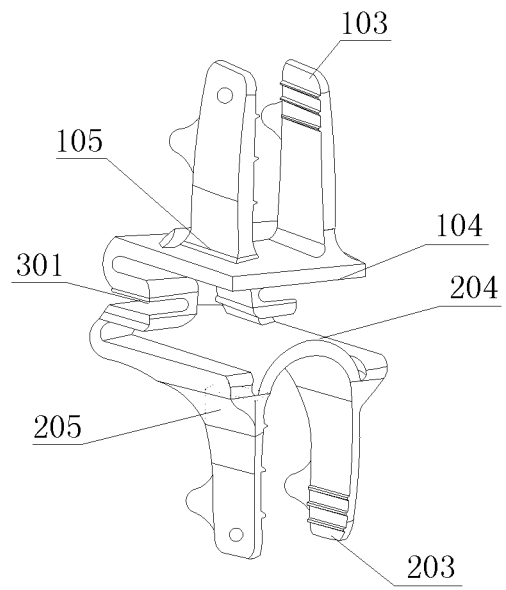
FIG. 8 is a schematic diagram illustrating a first side wing connected to a base plate and a second side wing connected to a curved base plate according to Example Two of the present disclosure.

Further, as shown in FIGS. 6-8, the first fixing part 1 includes two first side wings 103, a base plate 104 and a first fastening structure 105, the two first side wings 103 are movably connected to the base plate 104 through the first fastening structure 105, the first clamping teeth 101 are arranged on an inner side of each first side wing 103, the fixing hole 5 is arranged on an end of each first side wing 103, a lower side of each first side wing 103 is provided with a first curved protrusion 102, and the base plate 104 is provided with one or more barbs 6. The second fixing part includes two second side wings 203, a curved base plate 204 and a second fastening structure 205, the two second side wings 203 are movably connected to the curved base plate 204 through the second fastening structure 205, the second clamping teeth 201 are arranged on an inner side of each second side wing 203, the fixing hole 5 is arranged on an end of each second side wing 203, a lower side of each second side wing 203 is provided with a second curved protrusion 202, and the curved base plate 204 is provided with one or more barbs 6.

Further, first clamping teeth 101 and the second clamping teeth 201 extend in a direction parallel to and/or perpendicular to a longitudinal direction of a spinous process.

Figure 11:
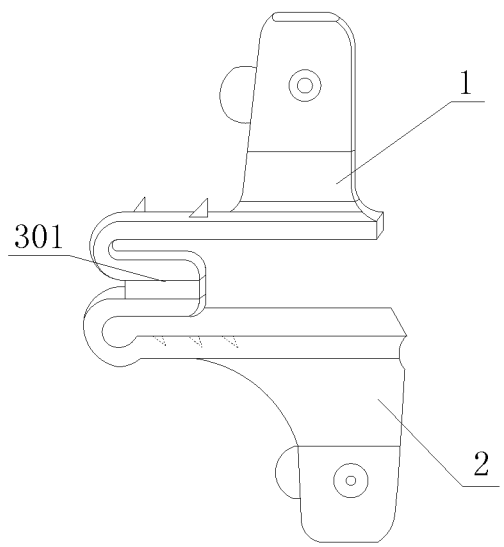
FIG. 11 is a schematic diagram illustrating a U-shape structure including a circular structure according to Example Two of the present disclosure.
Figure 12:
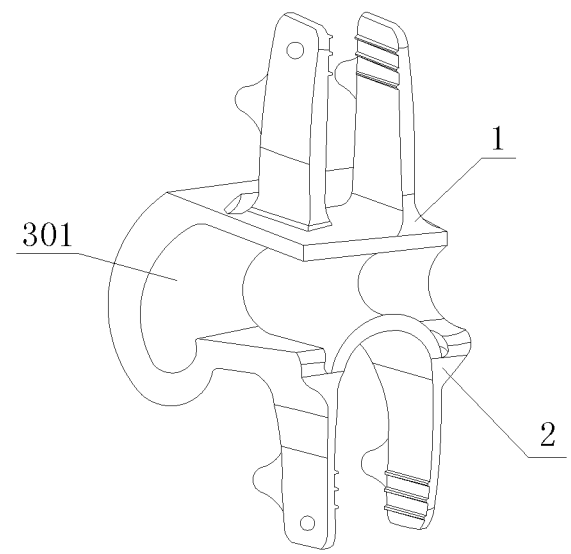
FIG. 12 is schematic diagram illustrating an interspinous omnidirectional dynamic stabilization device with only one U-shaped structure according to Example Two of the present disclosure.
Figure 13:
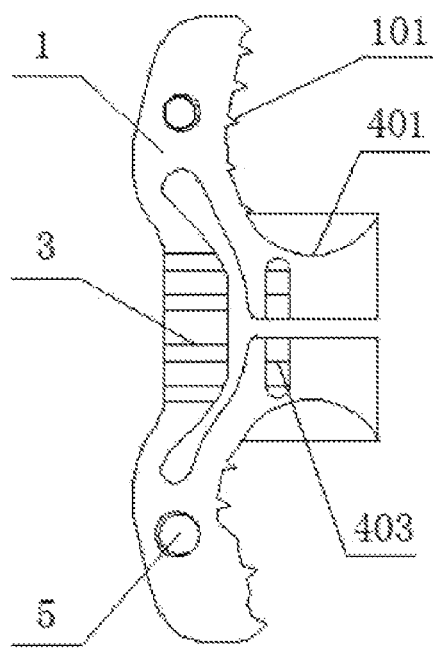
FIG. 13 is a front view of a first fixing part according to Example Three of the present disclosure.

The elastic structure 3 is arranged two sides between the first fixing part 1 and the second fixing part 2, or at the middle between the first fixing part 1 and the second fixing part 2, made up of one or more U-shaped structures 301 connected to each other. The U-shaped structure 301 is internally provided with a circular or arc structure, the U-shaped structure 301 has a straight portion with a length within a range from 0 to 15 mm, and when the length of the straight portion is 0 mm, the U-shaped structure 301 is replaced with a circular or arc structure. The U-shaped structure 301 includes a vertical U-shaped structure with an opening formed upwardly or downwardly, a horizontal U-shaped structure with an opening formed inwardly or outwardly, a combination of the vertical U-shaped structure and the horizontal U-shaped structure, or a horizontal U-shaped structure formed by a concave arc or convex arc connected by sides of one or more vertical U-shaped structures, with an opening formed inwardly or outwardly. FIG. 11 shows a U-shaped structure 301 including a circular structure, while FIG. 12 shows a U-shaped structure 301 as a arc structure directly.

Figure 9:
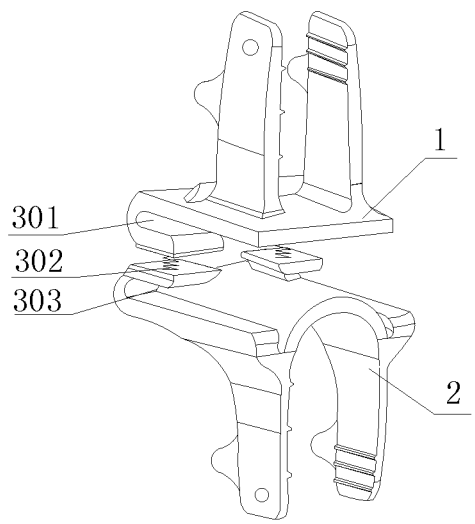
FIG. 9 is a schematic diagram illustrating both ends of a spring connected to a U-shaped structure according to Example Two of the present disclosure.
Figure 10:
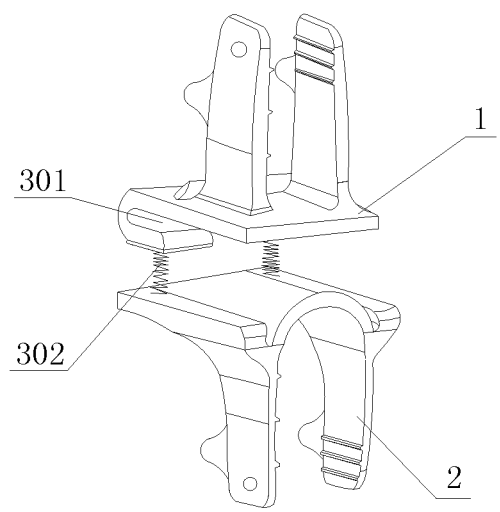
FIG. 10 is a schematic diagram illustrating one end of a spring connected to a U-shaped structure and the other end of the spring connected to a second fixing part according to Example Two of the present disclosure.

As shown in FIGS. 9-10, the elastic structure 3 includes a spring 302, both ends of the spring 302 are connected to two sides between the first fixing part 1 and the second fixing part 2 respectively, or connected to the middle between the first fixing part 1 and the second fixing part 2, or connected to the U-shaped structure 301 respectively, or one end of the spring 302 is connected to the U-shaped structure, and the other end of the spring is connected to the first fixing part 1 or the second fixing part 2. FIG. 9 shows a spring 302 both ends of which are connected to the middle between the first fixing part 1 and the second fixing part 2, and FIG. 10 shows a spring 302 in which one end is connected to the U-shaped structure and the other end is connected to the second fixing part 2.

When the interspinous omnidirectional dynamic stabilization device in this example is to be implanted in to the body of a patient suffered from a degenerative cervical or lumbar vertebra disease, the supraspinal ligament may not be incised, while the whole or part of the interspinal ligament may be removed. Upper and lower processes may be retracted to increase the intervertebral space. Then the mold is tested. If the test is successful, the elastic structure 3, the base plate 104 and the curved base plate 204 of the interspinous omnidirectional dynamic stabilization device may be inserted from one side of the intervertebral space into the opposite side of the intervertebral space. The first fixing part 1 and the second fixing part 2 may be connected and integrated to the elastic structure 3, the base plate 104 and the curved base plate 204 through the first fastening structure. The assembled interspinous omnidirectional dynamic stabilization device is inserted into the intervertebral space from the tail of the spinous process towards the root of the spinous process. By means of the elasticity of the first curved protrusion 102 at the lower end of the first fixing part 1 and the second curved protrusion 202 at the lower end of the second fixing part 2 during the inserting process, the first fixing part 1 and the second curved protrusion 202 may stretch automatically to be fastened to the upper and lower spinous processes respectively during the implantation of the interspinous omnidirectional dynamic stabilization device, to complete the installation. The first fixing part 1 and the second fixing part 2 may be further fastened to the spinous process and/or supraspinal ligament by suture, screw or metal wire passing the fixing holes 5 in the first fixing part 1 and the second fixing part 2. The barbs 6 at the bottom of the first fixing part 1 and the second fixing part 2 are hooked at the spinous processes, to prevent the first fixing part 1 and the second fixing part 2 from slipping backwards. In order to ensure the fastness of the barb 6, the spinous process may be reshaped appropriately. After the interspinous omnidirectional dynamic stabilization device is firmly fixed between the spinous processes, the supraspinal ligament may be sutured. In this example, the first fixing part 1 and the second fixing part 2 use fastening structures that are removable flexibly, so the supraspinal ligament may not be sutured or removed during surgery.

Example Three

In this example, the first fixing part 1 and the second fixing part 2 are two semi-U-shaped structures, and the connecting structure 4 connecting the two semi-U-shaped structures includes a holder 401 and a connecting plate 402.

As shown in FIGS. 13-25, the includes a first fixing part 1, a second fixing part 2, an elastic structure 3 and a connecting structure 4. The elastic structure 3 is arranged at the middle of the first fixing part 1 and the second fixing part 2. the first fixing part 1 and the second fixing part 2 are two semi-U-shaped structures. The first fixing part 1 is connected to the second fixing part 2 through the connecting structure 4 and the elastic structure 3. The connecting structure 4 may be strengthened by deforming the connecting structure 4 with an anti-off screw or bender after connection.

Further, the connecting structure 4 is made up of a holder 401 and a connecting plate 402, the holder 401 is arranged at the middle of the first fixing part 1, the holder 401 is in hollow structure, and the connecting plate 402 is arranged at the middle of the second fixing part. A distal end of the connecting plate 402 is provided with a screw hole or grooved portion 404, the holder 401 is provided with a screw hole or slotted hole 403. There are two pairs of the holder 401 and the connecting plate 402. The screw hole of the connecting plate 402 corresponds to the crew hole of the holder 401 when the connecting plate 402 is inserted into the holder 401, and the connecting plate 402 and the holder 401 are connected and integrated by a screw. Alternatively, the connecting plate 402 is fastened to the holder 401 by inserting the connecting plate 402 into the holder 401, and inserting a bender through the slotted hole in the holder 401 to bend and deform the grooved portion on the connecting plate 402, the first fixing part 1 and the second fixing part 2 in semi-U-shape form an entire U-shaped structure after connection, and the barb 6 of the first fixing part 1 is hooked at the root of the spinous process.

Figure 14:
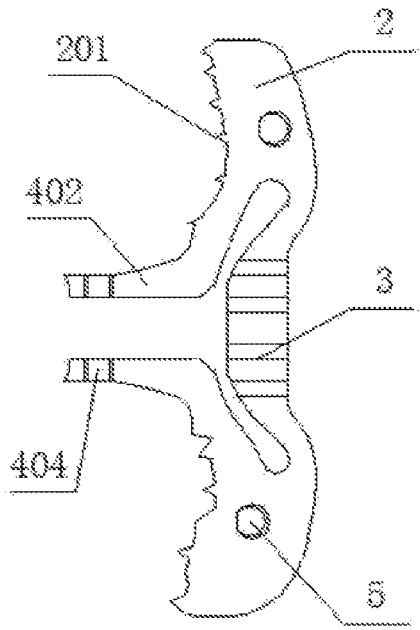
FIG. 14 is a schematic diagram illustrating a second fixing part connected to a connecting plate through an arc connection according to Example Three of the present disclosure.
Figure 15:
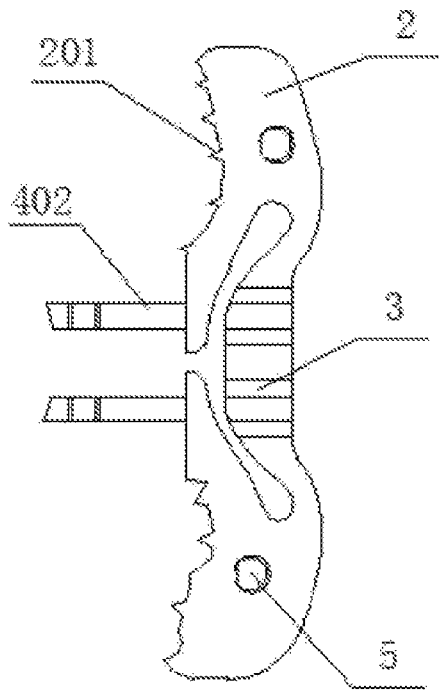
FIG. 15 is a schematic diagram illustrating a second fixing part connected to a connecting plate through a vertical connection according to Example Three of the present disclosure.
Figure 16:
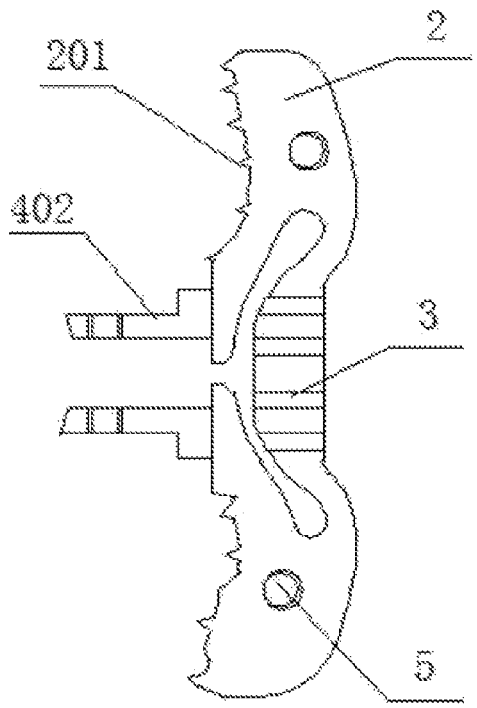
FIG. 16 is a schematic diagram illustrating a ladder-shaped connecting plate according to Example Three of the present disclosure.

Further, the connecting plate 402 may be arc-shaped as shown in FIG. 14, column-shaped as shown in FIG. 15, or ladder-shaped as shown in FIG. 16.

Further, each of the first fixing part 1, the second fixing part 2, the holder 401 and the connecting plate 402 is provided with at least one fixing hole 5, for accessorial fixation with medicinal non-absorbable suture, metal wire, anchor, screw or polyethylene material. The bottom of the first fixing part 1 is provided with one or more barbs 6, both sides of the first fixing part 1 are provided with first clamping teeth 101, both sides of the second fixing part 2 are provided with second clamping teeth 201, and first clamping teeth 101 and the second clamping teeth 201 extend in a direction parallel to and/or perpendicular to a longitudinal direction of a spinous process.

Figure 17:
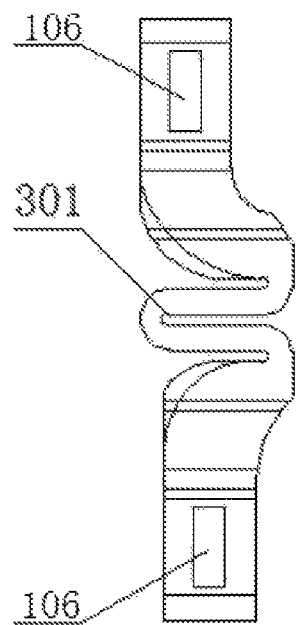
FIG. 17 is a schematic diagram illustrating a position of an inserting hole according to Example Three of the present disclosure.
Figure 18:
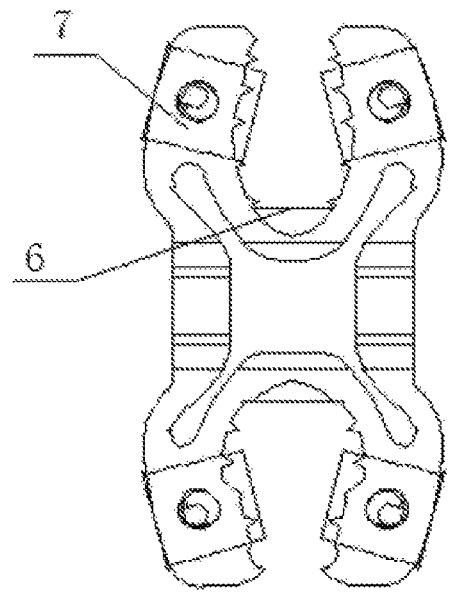
FIG. 18 is a schematic diagram illustrating a movable plate after assembly according to Example Three of the present disclosure.
Figure 19:
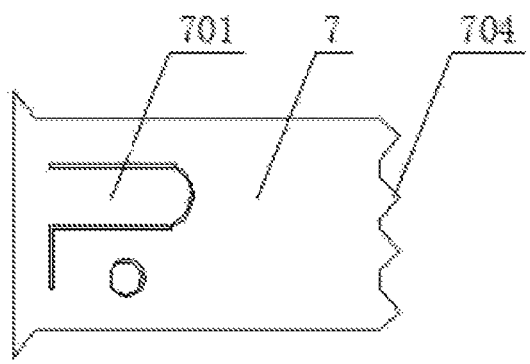
FIG. 19 is a front view of the movable plate according to Example Three of the present disclosure.

As shown in FIG. 17, each semi-U-shaped structure of the first fixing part (1) and the second fixing parts 2 is provided with a through inserting hole 106, and the direction of the inserting hole 106 is perpendicular to or not perpendicular to an external surface of the first fixing part 1 or the second fixing part. A movable plate 7 is mounted within the inserting hole 106, the movable plate 7 is provided with a prefabricated anti-receding plate 701, a screw hole and a convex tooth 702, the screw hole and the convex tooth 702 are arranged on any side of the movable plate 7. The movable plate 7 has a head end formed as a slope surface, the slope surface is provided with inserting teeth 704, the movable plate 7 has a tail end provided with a boss 703, and the boss 703 is arranged on any side of the movable plate 7. The screw hole and convex tooth 702 of the movable plate 7 are adapted to abut against an inner surface of each of the first fixing part 1 and the second fixing part 2 when being implanted into a human body. The movable plate 7 is adapted to be further inserted into the inserting hole 106 during operation, and screws are adapted to be screwed into the screw hole or the prefabricated anti-receding plate 701 is adapted to be bent with a bender to prevent the movable plate 7 from receding. When the movable plate 7 is formed into a cone without a convex tooth 702, the movable plate 7 is not mounted within the inserting hole 106 in advance, and is adapted to be inserted into the inserting hole 106 during operation, and screws are adapted to be screwed into the screw hole or the prefabricated anti-receding plate 701 is adapted to be bent with a bender to prevent the movable plate 7 from receding.

Figure 24:
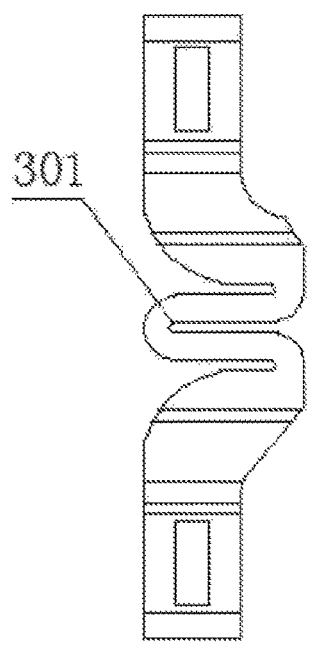
FIG. 24 is a schematic diagram illustrating a U-shaped structure without a circular hole at its bottom according to Example Three of the present disclosure.
Figure 25:
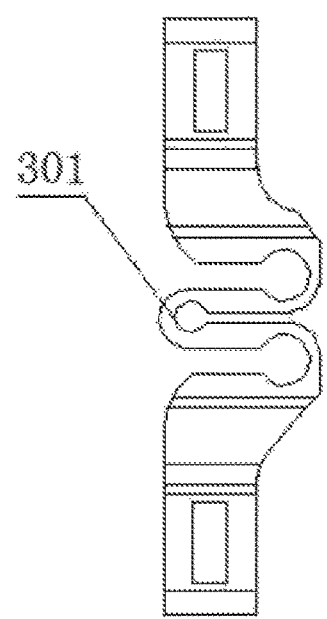
FIG. 25 is a schematic diagram illustrating a U-shaped structure with a circular hole at its bottom according to Example Three of the present disclosure.

Further, as shown in FIGS. 23-25, the elastic structure 3 is made up of one or more U-shaped structures 301 connected to each other. The U-shaped structure 301 is internally provided with a circular or arc structure, the U-shaped structure 301 has a straight portion with a length within a range from 0 to 15 mm, and when the length of the straight portion is 0 mm, the U-shaped structure 301 is replaced with a circular or arc structure. The U-shaped structure 301 includes a vertical U-shaped structure with an opening formed upwardly or downwardly, a horizontal U-shaped structure with an opening formed inwardly or outwardly, a combination of the vertical U-shaped structure and the horizontal U-shaped structure, or a horizontal U-shaped structure formed by a concave arc or convex arc connected by sides of one or more vertical U-shaped structures, with an opening formed inwardly or outwardly.

When the interspinous omnidirectional dynamic stabilization device in this example is to be implanted in to the body of a patient suffered from a degenerative cervical or lumbar vertebra disease, the sclerotin of the spinous process may be reshaped, and upper and lower processes are retracted to increase the intervertebral space. Then test molds. If the test is successful, the first fixing part 1 may be inserted into the intervertebral space close to the root of the spinous process from the supraspinal ligament on one side of the spinous process, with a longitudinal compressor pressing the elastic structure. Then take out the longitudinal compressor, and test molds. If the test is successful, the second fixing part 2 may be inserted into the intervertebral space from other side of the spinous process. The first fixing part 1 and the second fixing part 2 may be clamped towards each other, until the connecting plate 402 of the connecting structure 4 inserted into and engaged with the holder 401 so that the first fixing part 1 is connected and integrated to the second fixing part 2. The screw hole or grooved portion 404 in the connecting plate 402 corresponds to the screw hole or slotted hole 403 in the holder 401. The connecting plate 402 may be connected and integrated to the holder 401 by a screw passing through the screw holes. Alternatively, the connecting plate 402 may be fastened to the holder 401 by inserting the connecting plate 401 into the holder 402, and inserting a bender through the slotted hole in the holder 401 to bend and deform the grooved portion on the connecting plate 402, the connecting plate 402 and the first fixing part 1 in semi-U-shape form an entire U-shaped structure after connection, and the barb 6 of the first fixing part 1 is hooked at the root of the spinous process. The medicinal non-absorbable suture, metal wire, anchor, screw or polyethylene material may be used for accessorial fixation by passing through the fixing holes 5 in the first fixing part 1, the second fixing part 2, the holder 401 and the connecting plate 402. If it is found that the fixation is not firm in the surgery, the movable plates 7 on both sides may be hit inwards, so that the inserting teeth 704 of the movable plates 7 may be further inserted into the sclerotin of the spinous process or vertebral plate, and the tail of the movable plate 7 may be further inserted into the inserting hole 106. Then screws may be screwed into the screw holes or the prefabricated anti-receding plate may be bent with a bender to prevent the movable plate 7 from receding. In this way, the first fixing part 1 and the second fixing part 2 may be firmly implanted into the body of the patient suffered from a degenerative cervical or lumbar vertebra disease by the first clamping teeth 101 on the first fixing part 1, the second clamping teeth 201 on the second fixing part 2 and the connecting plate 402 on the U-shaped structure.

In the above Examples One to Three, each U-shape structure 301 has a same or different height, size, plate thickness or distance between plates, and plates on both sided of each U-shape structure 301 are parallel or not parallel to each other. Different portions of the first fixing part 1 has a same or different thickness or height, different portions of the second fixing part (2) has a same or different thickness or height, the first fixing part 1 and the second fixing part 2 have a same or different thickness or height, and plates of the first fixing part 1 and the second fixing part 2 have a same or different thickness or height. The portion of the first fixing part 1 or the second fixing part 2 attached to the spinous process or vertebral laminae is a flat plane or a curved plane. The surfaces of both the first fixing part 1 and the second fixing part 2 are coated with a material to induce the formation of bone therein, or processed to be porous or threaded.

The interspinous omnidirectional dynamic stabilization device in any one of Examples One to Three may be made of a biomedical polymeric material, a biomedical metallic material or both. The biomedical polymeric material may include one or more of polyethylene, polymethyl methacrylate (PMMA), biodegradable polymer (polylactic acid or chitin), or Peek material. The biomedical polymeric material may include one or more of biomedical stainless steel (for example, Fe-1 8Cr-14Ni-3Mo), cobalt-base alloy, titanium-base alloy (for example, Ti-6AL-4V), shape memory alloy (for example, nickel-titanium memory alloy), tantalum, and niobium. The titanium alloy is preferred, since it is easy to produce and brings less rejection reaction. The pure titanium and stainless steel are also preferred.

The interspinous omnidirectional dynamic stabilization device in any one of Examples One to Three may have different dimensions to be applicable to different applications or subjects. For example, the total length may be within a range from 8 mm to 80 mm, preferably, a range from 35 mm to 55 mm, which is more applicable to the skeleton of a middle-aged and aged person. The inner distance between two ends of the opening of each of the first fixing part 1 and the second fixing part is within a range from 6 mm to 18 mm, preferably, a range from 6 mm to 16 mm, which is more applicable to the skeleton of most people. The U-shape structure may have a height at a range from 6 mm to 30 mm, a thickness at a range from 0.4 mm to 3 mm, which may ensure the stability, and a width at a range from 6 mm to 30 mm, which may match the inner distance between two ends of the opening.

For the interspinous omnidirectional dynamic stabilization device according to the present disclosure, the first fixing part 1 and the second fixing part 2 are fastened to two adjacent spinous processes respectively, and mounted into the space between the two adjacent spinous processes entirely. Compared with the Coflex system, the bards 6 on the first fixing part 1 and the second fixing part 2 may be positioned deeper, and the rotating force may mainly apply on the root of the spinous process or the vertebral plate in which the sclerotin is stronger than other parts of the spinous process, so the risk of the fracture of the spinous process during the movement of the lumbar vertebra may be reduced, and the risk of damaging the dura mate may be also reduced since the device is not forced to be close to the dura mater during installation. The sagittal rotation center of the spine is not changed artificially, so the device has a strong ability of elasticity attenuation resistance, and is able to provide persistent, good vertical support at the root of the spinous process. Further, The interspinous omnidirectional dynamic stabilization device according to the present disclosure is movable in all directions when mounted on the skeleton, while the Coflex system only provides a single direction movement, which may limit the physiological activities of the human body greatly. The side wing of the Coflex system is a flat plate structure, and the surface of the spinous process is in the raised structure which is thick in the middle and thin in the both sides, so the surface of the spinous process should be reshaped during installation. In the interspinous omnidirectional dynamic stabilization device according to the present disclosure, for example, in Example Two, each of the first side wing 103 of the first fixing part 1 and the second side wing 203 of the second fixing part 2 is provide to be curved in the middle, so the surface of the spinous process should not be reshaped during the implantation of the device, to simplify the surgical operation and keep the sclerotin of the spinous process as much as possible.

Further, in the interspinous omnidirectional dynamic stabilization device according to the present disclosure, each of the first fixing part 1 and the second fixing part 2 is provided with an upward or downward opening for clamping the spinous process, and can be fixed with suture, screw or metal wire through the fixing holes 5 in the first side wing 103 and the second side wing 203. The elastic structure 3 is adapted to facilitate the elastic movement, for example, a movement of sagittal flexion, extension, and lateral curvature, and coronal or sagittal rotation of the interspinous omnidirectional dynamic stabilization device. The device thus assists to achieve the movement of the spine in all directions, and achieve the dynamic stabilization for the movement in all directions.

The above are preferred embodiments of the invention described in detail, and should not be deemed as limitations to the scope of the present invention. It should be noted that variations and improvements will become apparent to those skilled in the art to which the present invention pertains without departing from its spirit and scope. Therefore, the scope of the present disclosure is defined by the appended claims.

What is claimed is:

1. An interspinous omnidirectional dynamic stabilization device, comprising a first fixing part (1), a second fixing part (2), a connecting structure (4) and an elastic structure (3), wherein the first fixing part (1) and the second fixing part (2) are fixedly connected to each other through the connecting structure (4) and elastic structure (3), bottoms of the first fixing part (1) and the second fixing part (2) are provided with one or more barbs (6), the elastic structure (3) is made up of one or more U-shaped structures (301) connected to each other, and the first fixing part (1) and the second fixing part (2) are provided with fixing holes (5) respectively; wherein the first fixing part (1) and the second fixing part (2) are two semi-U-shaped structures, each semi-U-shaped structure is provided with a through inserting hole (106), the direction of the inserting hole (106) is perpendicular to or not perpendicular to an external surface of the first fixing part (1) or the second fixing part (2), a movable plate (7) is mounted within the inserting hole (106), the movable plate (7) is provided with a prefabricated anti-receding plate (701), a screw hole and a convex tooth (702), the screw hole and the convex tooth (702) are arranged on any side of the movable plate (7), the movable plate (7) has a head end formed as a slope surface, the slope surface is provided with inserting teeth (704), the movable plate (7) has a tail end provided with a boss (703), the boss (703) is arranged on any side of the movable plate (7), the screw hole and convex tooth (702) of the movable plate (7) are adapted to abut against an inner surface of each of the first fixing part (1) and the second fixing part (2) when being implanted into a human body, the movable plate (7) is adapted to be further inserted into the inserting hole (106) during operation, and screws are adapted to be screwed into the screw hole or the prefabricated anti-receding plate (701) is adapted to be bent to prevent the movable plate (7) from receding; and when the movable plate (7) is formed into a cone without a convex tooth (702), the movable plate (7) is not mounted within the inserting hole (106) in advance, and is adapted to be inserted into the inserting hole (106) during operation, and screws are adapted to be screwed into the screw hole or the prefabricated anti-receding plate (701) is adapted to be bent to prevent the movable plate (7) from receding.

2. The interspinous omnidirectional dynamic stabilization device of claim 1, wherein the connecting structure (4) is made up of a holder (401) and a connecting plate (402), the holder (401) is arranged at the middle of the first fixing part (1), the holder (401) is in hollow structure, the connecting plate (402) is arranged at the middle of the second fixing part, a distal end of the connecting plate (402) is provided with a screw hole or grooved portion (404), the holder (401) is provided with a screw hole or slotted hole (403), there are two pairs of the holder (401) and the connecting plate (402), the screw hole of the connecting plate (402) corresponds to the screw hole of the holder (401) after the connecting plate (402) is inserted into the holder (401), and the connecting plate (402) and the holder (401) are connected and integrated by a screw, alternatively, the connecting plate (402) is fastened to the holder (401) by inserting the connecting plate (402) into the holder (401), and bending and deforming the grooved portion on the connecting plate (402), the first fixing part (1) and the second fixing part (2) in semi-U-shape form an entire U-shaped structure after connection, and the barb (6) of the first fixing part (1) is configured to be hooked at the root of the spinous process.

3. An interspinous omnidirectional dynamic stabilization device, comprising a first fixing part (1), a second fixing part (2), a connecting structure (4) and an elastic structure (3), wherein the first fixing part (1) and the second fixing part (2) are fixedly connected to each other through the connecting structure (4) and elastic structure (3), bottoms of the first fixing part (1) and the second fixing part (2) are provided with one or more barbs (6), the elastic structure (3) is made up of one or more U-shaped structures (301) connected to each other, and the first fixing part (1) and the second fixing part (2) are provided with fixing holes (5) respectively; wherein the connecting structure (4) is made up of a holder (401) and a connecting plate (402), the holder (401) is arranged at the middle of the first fixing part (1), the holder (401) is in hollow structure, the connecting plate (402) is arranged at the middle of the second fixing part, a distal end of the connecting plate (402) is provided with a screw hole or grooved portion (404), the holder (401) is provided with a screw hole or slotted hole (403), there are two pairs of the holder (401) and the connecting plate (402), the screw hole of the connecting plate (402) corresponds to the screw hole of the holder (401) after the connecting plate (402) is inserted into the holder (401), and the connecting plate (402) and the holder (401) are connected and integrated by a screw, alternatively, the connecting plate (402) is fastened to the holder (401) by inserting the connecting plate (402) into the holder (401), and bending and deforming the grooved portion on the connecting plate (402), the first fixing part (1) and the second fixing part (2) in semi-U-shape form an entire U-shaped structure after connection, and the barb (6) of the first fixing part (1) is configured to be hooked at the root of the spinous process.

\* \* \* \* \*